United States Patent [19]
Bailey

[11] Patent Number: 6,017,333
[45] Date of Patent: *Jan. 25, 2000

[54] IRRIGATING LAPAROSCOPIC CANNULA

[76] Inventor: Robert W. Bailey, 8 Culmore Ct., Timonium, Md. 21093

[ * ] Notice: This patent is subject to a terminal disclaimer.

[21] Appl. No.: 08/421,704

[22] Filed: Apr. 13, 1995

[51] Int. Cl.[7] ................................................. A61M 5/00
[52] U.S. Cl. ..................... 604/264; 604/151; 600/157; 600/158
[58] Field of Search ..................... 600/101, 104, 600/114, 121, 123, 153, 155–9, 184, 186–7, 203–5; 604/19, 27, 43, 131, 140–1, 149–153, 158, 164–5, 171, 173, 181, 257–8, 264, 268, 275–6, 272, 273–4, 280, 283, 44, 523, 533, 534, 535, 537, 539

[56] References Cited

U.S. PATENT DOCUMENTS

| | | | |
|---|---|---|---|
| 3,720,203 | 3/1973 | Brown | 600/156 |
| 4,548,197 | 11/1985 | Kinashita | 604/27 |
| 4,669,463 | 6/1987 | McConnell | 604/283 |
| 4,690,672 | 9/1987 | Veltrop | 604/43 |
| 4,919,113 | 4/1990 | Sakamoto et al. | 600/155 |
| 5,013,296 | 5/1991 | Buckberg et al. | 604/44 |
| 5,025,778 | 6/1991 | Silverstein et al. | 600/104 |
| 5,167,220 | 12/1992 | Brown | 604/280 |
| 5,219,335 | 6/1993 | Willard et al. | 604/43 |
| 5,339,800 | 8/1994 | Wiita et al. | 600/157 |
| 5,372,582 | 12/1994 | Skrabal et al. | 604/44 |
| 5,386,817 | 2/1995 | Jones | 600/158 |
| 5,458,633 | 10/1995 | Bailey | 604/164 |
| 5,487,376 | 1/1996 | Yabe et al. | 600/158 |
| 5,489,256 | 2/1996 | Adair | 600/153 |
| 5,575,756 | 11/1996 | Karasawa et al. | 600/157 |
| 5,766,217 | 6/1998 | Christy | 606/148 |

OTHER PUBLICATIONS

J. Madeleine Nash, "The Kindest Cuts of All", Mar. 23, 1992, Time, pp. 52–53.

*Primary Examiner*—Ronald K. Stright, Jr.
*Attorney, Agent, or Firm*—Robert S. Lipton, Esq.; Lipton, Weinberger & Husick

[57] ABSTRACT

A trocar assembly consisting of a trocar in a central opening in a cannula. The cannula is provided with at least one separate passage running parallel to the central passage. The separate passage is connected to a source of cleansing fluid and a pump for pumping fluid through the separate passage. The separate passage terminates in an orifice near the distal end of the central opening of the cannula. In operation, when the cannula is used to provide access for a laparoscope or other viewing instrument, the end of the viewing instrument may become clouded with moisture and other debris. In this case, the end of the viewing instrument may be withdrawn into the distal end of the cannula adjacent the fluid orifice. The pump is actuated and cleansing fluid is forced over the end of the instrument cleaning away the obstructing matter without removing the instrument from the cannula. Drying air can also be supplied to the instrument, either through the same or a different separate passage. The orifice can provide a concentrated stream or a diffuse spray and can be configured to discharge the fluid with a rearward component.

13 Claims, 4 Drawing Sheets

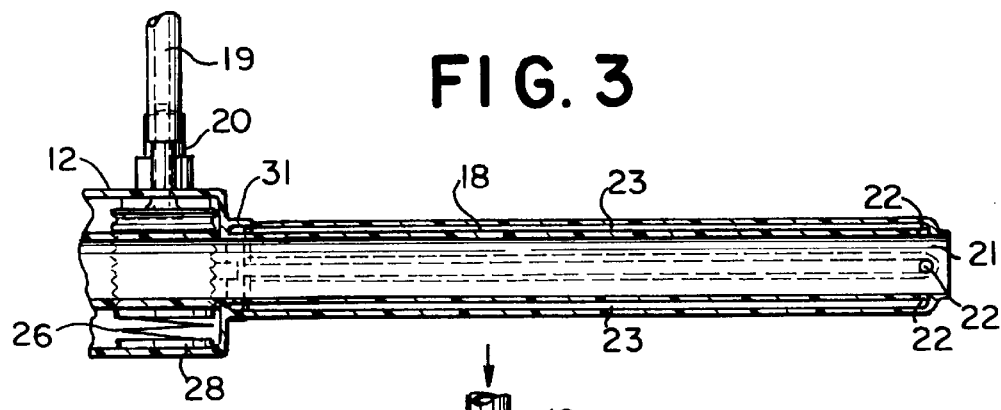
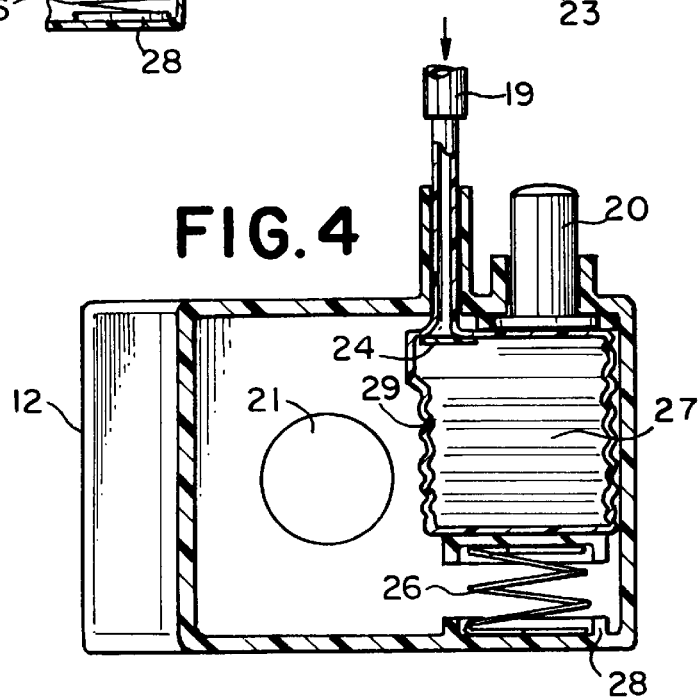
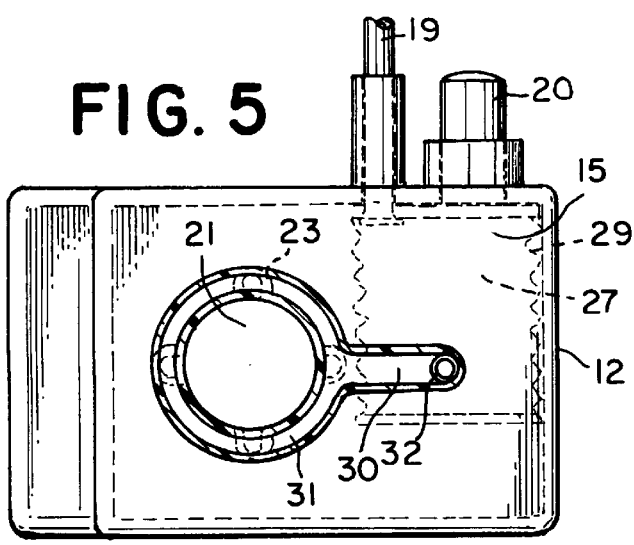
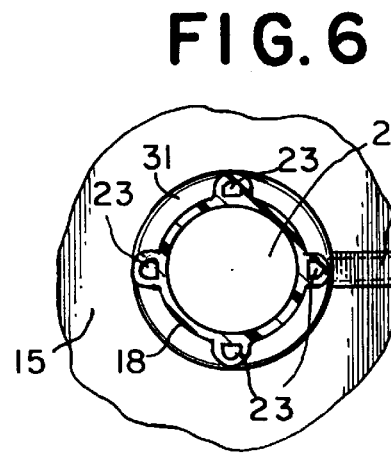

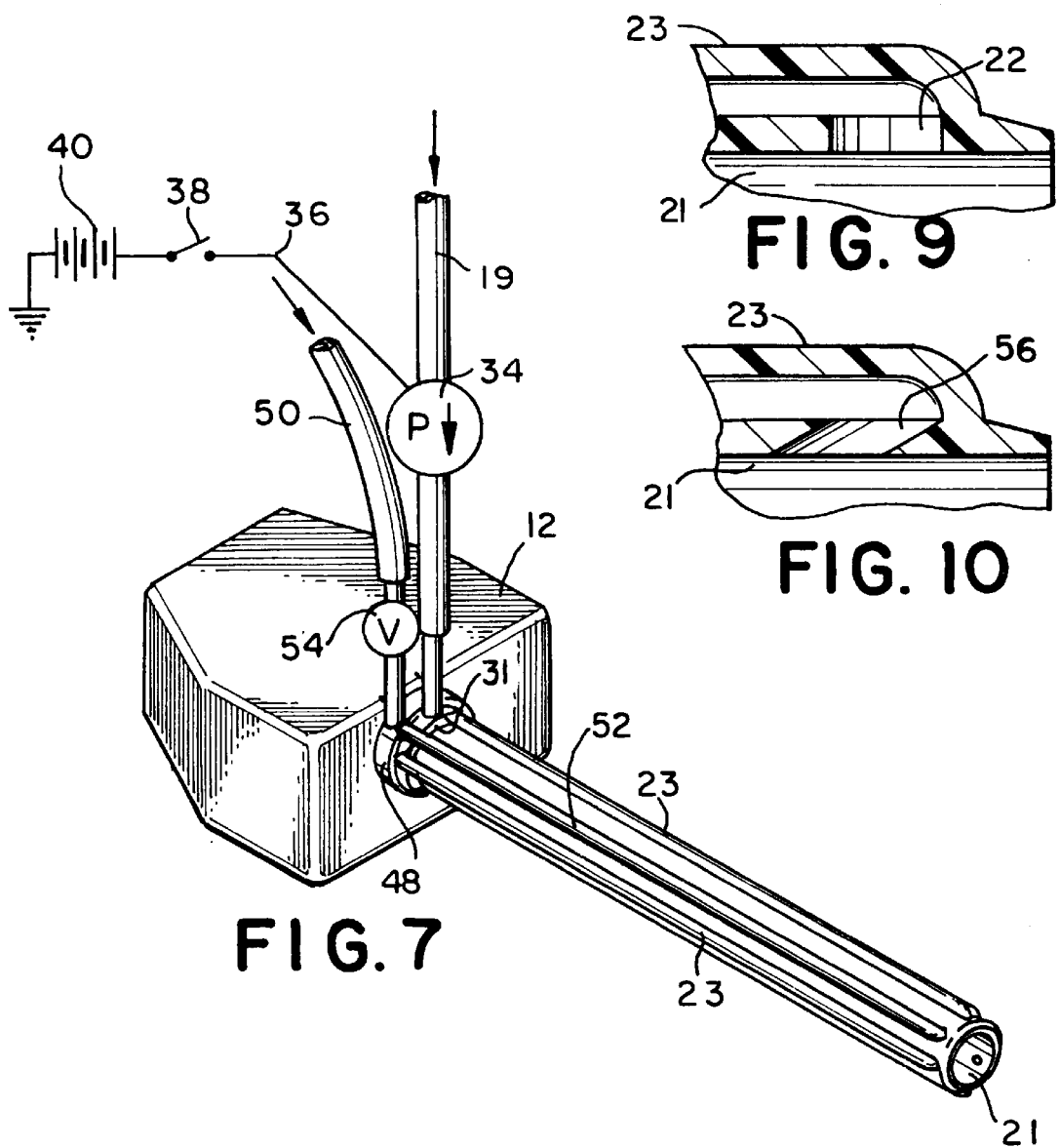
FIG. 7
FIG. 9
FIG. 10
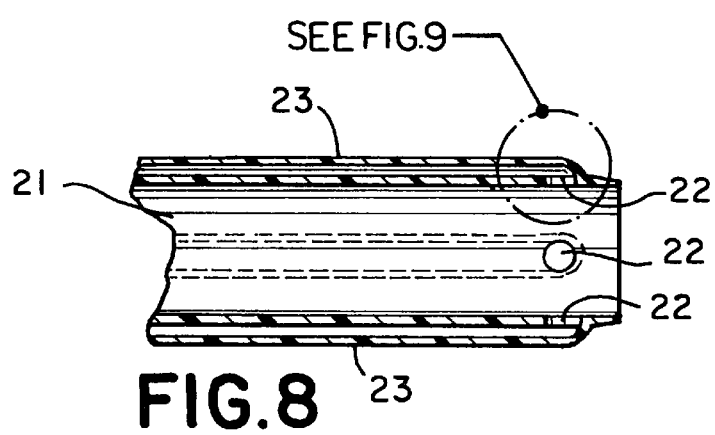
FIG. 8

IRRIGATING LAPAROSCOPIC CANNULA

BACKGROUND OF THE INVENTION

This invention relates in general to trocars for insertion into a body cavity for providing a conduit through the cavity wall to allow surgical procedures to be performed through the cannula without opening the cavity wall or to observe surgical procedures by means of a laparoscope inserted into the cannula of the trocar.

Such trocars typically consist of an outer cannula comprising a hollow tube through which an inner trocar is inserted. The inner trocar consists usually of a solid rod-like member having a sharp distal end for penetrating the wall of the body cavity. The trocar is inserted into a small incision in the body and the trocar is then placed in the incision and the inner trocar activated to penetrate the cavity wall. The inner cannula is then removed and the outer trocar is utilized to insert surgical instruments into the cavity or to insert a laparoscope into the cavity to enable the surgeon to observe the operation of other devices inserted into the body cavity through additional trocars in the body.

The laparoscope consists of an optical member which can conduct the image observed in the cavity to an external eyepiece or to an electronic display available to the surgeon. The laparoscope may also include a light source as well as other instruments required for the surgery to be performed.

One of the principal problems encountered in the use of such laparoscopes is that of clouding of the tip of the laparoscope from condensed moisture in the cavity or obscuring the end of the laparoscope by body fluids, blood or other organic material displaced by the surgical activity. The clouding may also be caused because of the temperature difference between the ambient air in the operating room and the temperature of the body. Typically, the temperature in the operating room is in the order of 20° C. (68° F.) while the temperature of the body cavity is in the order of 37° C. (98.6° F.). When the cooler instrument comes into contact with the warmer moist atmosphere of the body cavity, moisture from the atmosphere will condense on the end of the optical fiber fogging the view of the surgeon.

When the observing end of the optical fiber becomes obscured, either from bodily fluids or due to condensation, it is necessary to withdraw the laparoscope from the cannula and clean the end of the laparoscope. When the laparoscope is reinserted in the cannula it is often difficult to re-locate the exact field of the surgery thus extending the time for the procedure and frustrating the surgeon's efforts.

One solution to the condensation problem is to warm the laparoscope before inserting it in the cannula by immersing it in water at approximately body temperature or wrapping it in warm towels prior to use. While these actions may reduce or eliminate the condensation, they are not effective in preventing body fluids, blood and other organic matter within the body cavity from repeatedly obscuring the view of the surgeon.

In the prior art various devices have been described disclosing solutions to these problems. However, these solutions are generally complicated and expensive. For example, U.S. Pat. No. 5,225,001 discloses a device which incorporates as part of an endoscope an annular passage surrounding the optical fiber through which a cleansing fluid can be pumped using an electric actuator operating on a syringe located in the body of the device outside the body cavity. While this device is effective in cleaning the distal end of the optical fiber, it adds considerable additional complexity to the viewing instrument and no doubt increases its cost. Also, it does not efficiently clean the tip of the laparoscope as well as would be desired. Additionally, the inclusion of the annular channel within the viewing device requires a larger outside diameter for the instrument. In U.S. Pat. No. 5,167,220, a second tube is provided which is attached to the outer surface of the scope device for propelling a cleansing fluid across the viewing end of the fiber. This solution suffers from the same drawbacks as the previously described patent. In endoscopic instruments where substantial amounts of continuous irrigating fluid are required, there has been provided separate nozzles for directing some of the irrigating fluid across the viewing end of the optical fiber for clearing fluids and debris from the fiber. One such device is described in U.S. Pat. No. 3,835,842. However, again the cleansing function is incorporated as a part of the scope instrument with the above described disadvantages of complexity, lack of efficiency and additional cost.

SUMMARY OF THE INVENTION

In the present invention, there is disclosed a trocar assembly having an inner trocar for penetrating a body cavity through a surface incision. This inner trocar is contained in an outer cannula. The outer cannula is provided with one or more fluid passages extending along the length of the outer surface of the cannula.

These fluid passages are connected to a source of cleansing fluid connected to the base of the trocar assembly. These fluid conduits terminate near the distal end of the cannula in transverse openings connected to the interior opening of the cannula. A fluid source is provided and is connected to the base of the trocar assembly. There is provided within the base of the trocar assembly, a pump means for propelling cleansing fluid along the fluid passages and out of the transverse openings in the cannula.

These openings may provide for the ejection of the fluid as a spray or forceful narrow stream. The fluid may be ejected at different angles to increase the dispersion field. Thus, when the distal end of the optical fiber becomes obscured, It is only necessary to withdraw the optical instrument a few centimeters into the distal end of the cannula adjacent the transverse fluid openings. The fluid pump is then actuated and cleansing fluid, for example a saline solution, is directed across the end of the laparoscope from several directions to remove the obstructing material. By providing the cleansing facility in the cannula rather than as a part of the observing instrument, the observing instrument may be of a simpler design and likely of smaller diameter than if the cleansing apparatus was incorporated in the instrument. This feature can be easily incorporated into either reusable or disposable trocars without greatly increasing the cost or complexity of the trocar.

Air can also be passed through the passages which can be used to dry the cleansed laparoscope. If desired separate passages, openings and pumps can be provided for the air.

BRIEF DESCRIPTION OF THE DRAWINGS

FIG. 3 is a sectional view taken along line 3—3 of FIG. 2.

FIG. 4 is a sectional view taken along line 4—4 of FIG. 2.

FIG. 5 is a sectional view taken along line 5—5 of FIG. 2.

FIG. 6 is a sectional view taken along line 6—6 of FIG. 2.

FIG. 7 is an isometric view of an alternate embodiment of the invention.

FIG. 8 is an enlarged view of the distal end of the sectional view of FIG. 3.

FIG. 9 is an enlarged view of the orifices shown in FIG. 8.

FIG. 10 is another embodiment of the orifices shown in FIG. 9.

DETAILED DESCRIPTION OF THE INVENTION

Figure 1:
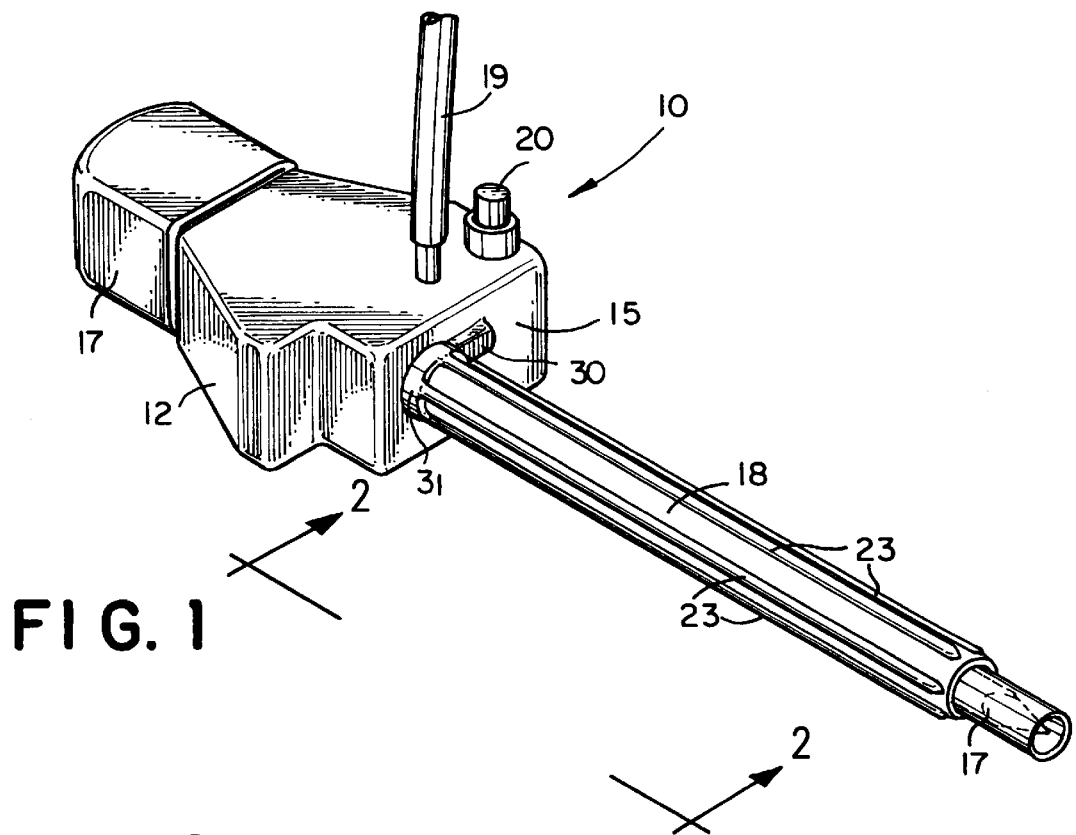
FIG. 1 is an isometric view of the invention.

Referring now to FIG. 1, there is shown at 10, an isometric view of an cleansing trocar assembly according to the invention. The trocar assembly consists of an inner trocar 17 for penetrating a body cavity through an incision and a trocar cannula having a proximate end 14 and a distal end 16. The assembly 10 includes a body 12 for supporting the inner-Troca 17. On the body 12 there is provided a conduit 19 connected to a source of cleansing fluid, for example a saline solution. Adjacent the conduit 19 there is provided an actuator button 20. The function of this button will be described in the detailed description of the operation of the device. Attached to the front surface 15 of the body 12 is a tube 18 which extends from the front body surface 15 to the distal end of the cannula.

Figure 2:
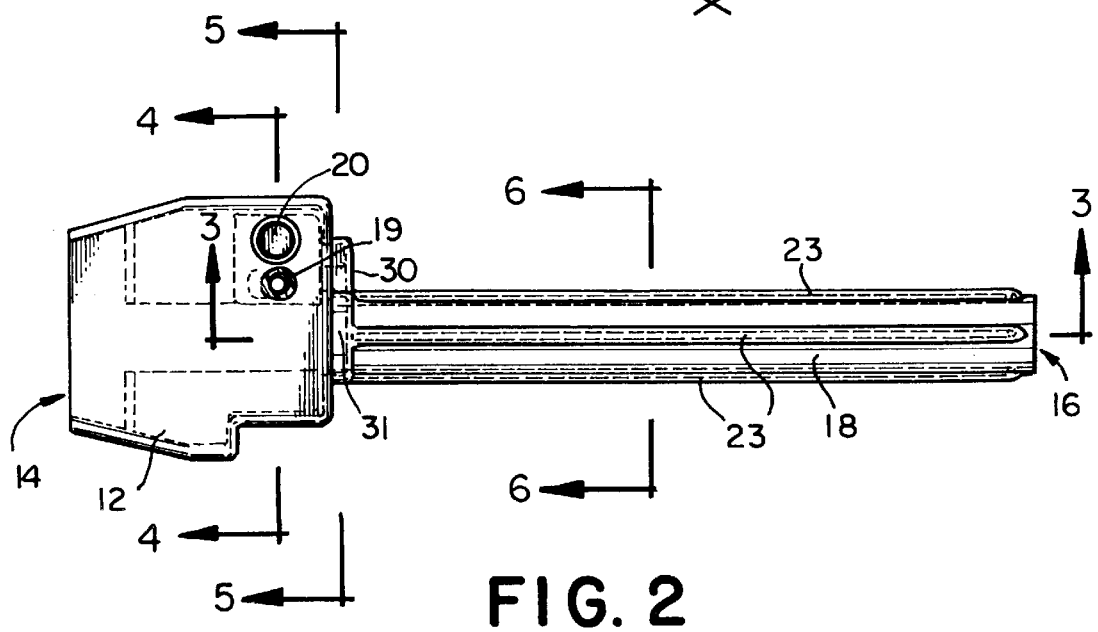
FIG. 2 is a plan view of the invention, partly in section taken along line 2—2 of FIG. 1.

Referring now to FIG. 2 there is shown a sectional view of the cannula of FIG. 1, taken along line 2—2 of FIG. 1. In this figure, the tube 18 is shown in cross section illustrating the central opening 21 of the cannula and the cleansing fluid passages 23 formed on the outside wall of the tube 18 and spaced approximately equally around the periphery of the tube 18. These passages 23 are connected at their proximate end to a source of cleansing fluid which will be described in detail in connection with the description of FIGS. 3,4 and 5. At their distal end these passages open in a transverse direction at orifices 22 to communicate with the central opening 21 near the distal end of the cannula. The distance from the orifices 22 to the distal end of the cannula for example, may be approximately 1 to 2 centimeters, but in a preferred embodiment are less than five millimeters from the distal end of the cannula. Referring now to FIGS. 3, 4 and 5, there are shown three sectional views through the cannula of the invention.

FIG. 3, taken along line 3—3 of FIG. 2 illustrates more clearly the location of the orifices 22 in relationship to the fluid passages 23 and the tube 18. In FIG. 4, a sectional view taken along line 4—4 of FIG. 2, there are shown the details of the mechanism for providing the cleansing fluid to the orifices 22. The cleansing fluid, a saline solution for example, enters the body 12 of the trocar assembly through conduit 19. At the end of the conduit 19 inside the body 12 is a check valve 24. This valve may be of any known design of check valves such as a flapper design or similar device. The purpose of this valve is to prevent the cleansing fluid and other fluids and matter from within the body cavity of the patient from returning back through the cannula and into the source of cleansing fluid. The cleansing fluid enters the body 12 through valve 24 into a pumping chamber 27. This chamber 27 is formed by a flexible bellows 29 supported on a spring assembly 28. The lower surface of the button 20 which extends through the top surface of the body 12, extends to the top of the bellows 29. The bellows 29 is supported on spring assembly 28 at its lower end. As can be seen, when the button 20 is depressed, the bellows 29 and the spring 26 will be compressed. When the button is released, the bellows and spring will return to their original expanded positions. The operation of this bellows assembly will be discussed in more detail in the description of the operation of the invention which follows.

Referring now to FIG. 5, there is shown a sectional view of the body 12 of the trocar assembly taken along line 5—5 of FIG. 2. There is shown a fluid opening 32 which connects to the pumping chamber 27 of the bellows 29. This opening 32 is connected by a passage 30 to a manifold 31 which,in turn, is connected to the fluid passages 23 of the cannula. FIG. 6, taken along line 6—6 of FIG. 2 illustrates more clearly the fluid passages 23 in the tube 18. FIG. 8 is an enlarged cross sectional detail of the distal end of the cannula shown in section in FIG. 3.

FIG. 7 illustrates an alternate embodiment of the invention shown in FIG. 1. In this embodiment, the button 20 and its associated mechanism including the bellows and spring have been eliminated. In their place there is provided an external pump mechanism 34 connected to a fluid source by conduit 19. This pump may be of any known type and is connected to a control device for causing the pump to supply irrigating fluid to the cannula. In FIG. 7 the control device is illustrated with an electrical connection 36 in which there is provided a switch 38. Switch 38 is connected to a power source 40 shown for example as a battery source. The switch 38 may be actuated by a button connected to the body of the trocar for operation by the surgeon, by a remote button operable by an assistant in the operating room at the request of the surgeon or may be a foot operated switch operated by the surgeon or an assistant.

The cleansed end of the laparoscope may be dried if desired by passing air through tube 19 instead of the liquid used for cleaning. In the alternative a separate air delivery system may be incorporated in the cannula. A source of pressurized air (or other gas(es)) may be connected to tube 50. Tube 50 is connected to an air valve 54 which is in turn connected to an air manifold 48. Air passages 52 in the cannula tube are connected to the air manifold 48. The air, or other gas, is directed toward the center of the cannula, to dry the end of the appropriately positioned laparoscope, through appropriate orifices.

The orifices for directing fluid toward the interior of the cannula tube are shown in FIGS. 8, 9 and 10. The orifices 22 in FIGS. 8 and 9 direct the fluid, i.e. the cleaning liquid or the air used for drying perpendicular to the center line of the cannula tube. The shape of the orifices will determine whether or not a concentrated forceful stream is ejected or whether a fine spray, in the case of a liquid, or a wide dispersion area in the case of a gas is ejected. In FIG. 10 an orifice 56 is shown directing the fluid in a rearward direction towards the proximate end of the assembly (i.e., the orifice 56 is oriented in a direction forming an acute angle with the passage). This will permit the fluid to more directly impact the appropriately positioned laparoscope, thus facilitating the cleaning or drying thereof.

In operation, the trocar assembly 10 is placed in contact with the patients' body at the point where entry is desired. The inner trocar 17 is placed in a small incision in the patient's skin and is actuated and made to pierce the body wall and provide access to the body cavity where a laparoscope is to be used. The inner trocar is removed from the trocar cannula and the laparoscope is inserted through the cannula into the body cavity. The laparoscope is then available to provide the surgeon with a view of the surgery to be performed by instruments inserted through other cannula at other locations on the patient.

As discussed in the background of the invention given above, if the laparoscope is at a temperature lower than that in the body cavity when it is inserted, the moisture in the body cavity will condense on the optical fiber of the laparoscope and will cloud the surgeons view of the operating area. Likewise, in the course of the surgical procedure, blood and other body fluids as well as protein material is dislodged and often partially or completely covers the viewing end of the laparoscope. If a prior art cannula is used, it becomes necessary to remove the laparoscope from the cannula, clean the viewing surface and reinsert the laparoscope into the cannula. It is then sometimes difficult to return the laparoscope exactly to its prior position and additional length is added to the time of the surgical procedure. When the cannula of the instant invention is used, if the viewing end of the laparoscope is clouded with moisture or other matter, it is only necessary to withdraw the laparoscope one or two centimeters into the distal end of the cannula to place it adjacent to the orifices 22 of the cannula. The fluid pumping mechanism is activated and a cleaning irrigation fluid is forced over the end of the laparoscope washing the obstructing material away. Since the laparoscope has been moved only a small distance from the desired location, it is easily returned to its original position in a very short time.

Figure 11:
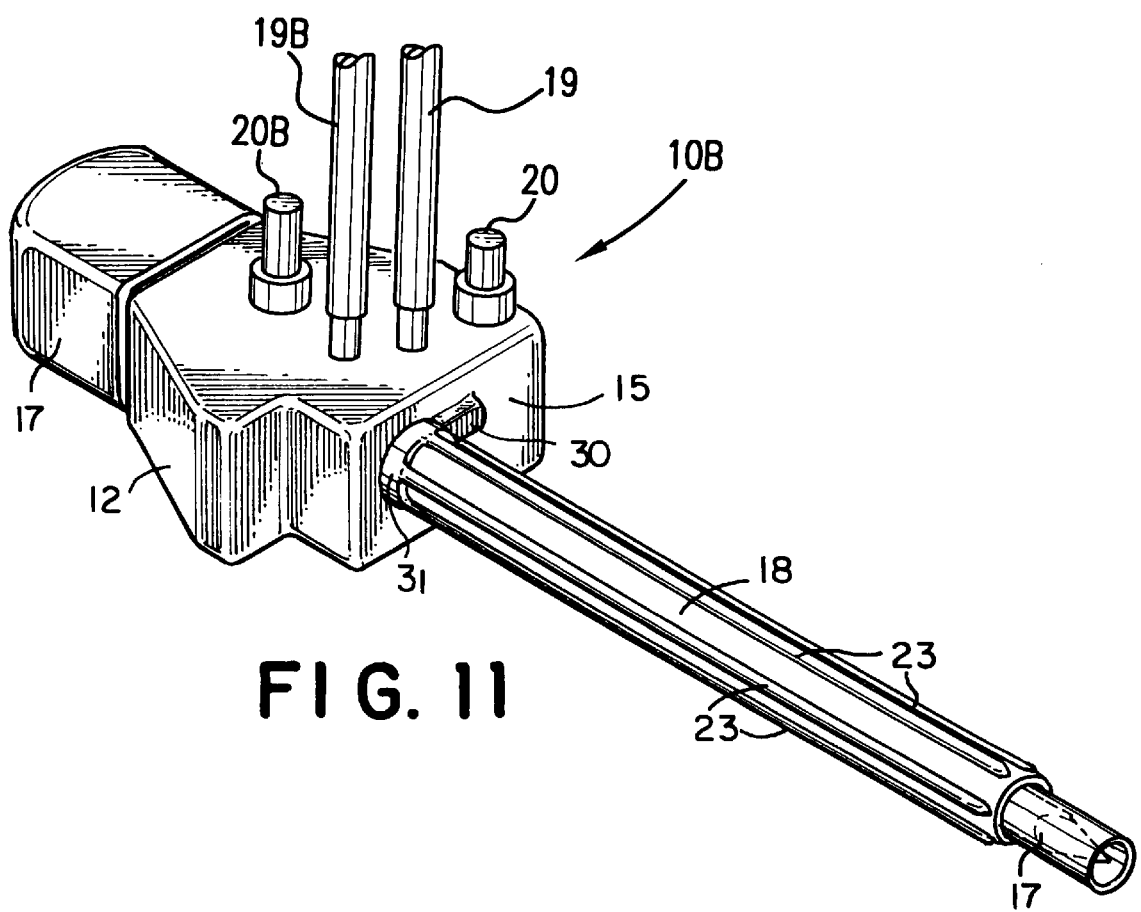
FIG. 11 is an isometric view of another embodiment of the invention illustrating multiple feed lines and control buttons.

As illustrated in FIG. 11, the cannula of FIG. 1 has been modified to include a means of injecting drying gas through at least one of said passages. Flexible conduit 19B is connected to a pump (not shown) that forces the drying gas through at least one of the passages. A button 20B, similar to button 20 for controlling the flow of a fluid, controls the flow of the drying gas.

Thus it can be seen that in this invention there is provided a cannula for a trocar which has the provision for cleaning the viewing end of an optical instrument easily and quickly without removing the instrument from the cannula. Providing the cleansing function in the cannula rather than in the optical instrument itself, a simpler less expensive instrument may be used. Because the cleansing feature is easily incorporated in the cannula it is adaptable to disposable as well as reusable trocars.

What is claimed is:

1. A trocar assembly comprising:
    a cannula having a proximate end, a distal end, a central opening extending along a longitudinal central axis of said cannula, an inner wall facing the central opening and an outside wall facing away from the central opening;
    an inner trocar mounted inside the central opening of the cannula, said inner trocar having a proximate end and a distal end;
    a body member that connects to the proximate end of said cannula;
    a conduit connected to said body member for supplying fluid to said cannula;
    fluid pumping means connected to said conduit for pumping fluid to said cannula;
    four fluid passages arranged approximately parallel to and separate from the central opening in said cannula, said passages arranged approximately equally around the periphery 90° apart and connected to said pumping means via said conduit near the proximate end of said cannula, said four fluid passages terminating in a respective orifice, said orifices opening into said central opening in said cannula, each of said orifices extending transverse to the axis of the central opening in said cannula and located near the distal end of said central opening, for cleaning medical instruments that are inserted through the central opening of said cannula,
    said four fluid passages being formed on the outside wall of said cannula, said at least one passage being permanently open for the flow of fluid to said orifice.

2. The trocar assembly according to claim 1 wherein said orifices are located less than 5 mm. from the distal end of said cannula.

3. The trocar assembly according to claim 1 wherein said fluid pumping means comprises:
    a mechanical pump connected to a power source; and
    switch means connected between said pump and said power source for energizing said pump, thereby propelling the fluid through said at least one passage.

4. The trocar assembly according to claim 1, wherein the orifices are is oriented substantially perpendicularly to the central axis of the cannula.

5. The trocar assembly according to claim 1, wherein said orifice is oriented in a direction forming an acute angle with the passage so that said fluid is directed in a rearward direction towards the proximate end of said assembly.

6. The trocar assembly of claim 1, wherein said fluid pumping means includes means for pumping to said four connected to said pumping means either a cleansing liquid, or a drying gas.

7. The trocar assembly of claim 1, wherein at least one of said four fluid passages is connected to means for pumping cleansing liquid and at least one of the other of said four fluid passages is connected to means for pumping drying gas.

8. A cleansing cannula having a proximate end and a distal end, a central opening extending along a central axis an inner wall facing the central opening and an outside wall facing away from the central opening, said cannula comprising:
    a body member;
    a conduit connected to said body member for supplying cleansing fluid to the cannula;
    cleansing fluid pumping means connected to said conduit for pumping cleansing fluid to said cannula;
    four fluid passages arranged approximately parallel to and separate from the central opening in said cannula, said four passages arranged approximately equally around the periphery 90° apart and connected to said pumping means via said conduit near the proximate end of said cannula, said four fluid passages each terminating in an orifice opening into said central opening in said cannula and extending transverse to the axis of the central opening in said cannula, said orifices being located near the distal end of said central opening for cleaning medical instruments that are inserted through the central opening of said cannula,
    said four passages being formed on the outside wall of said cannula, said four passages being permanently open for the flow of fluid to said orifice;
    each of said fluid passages terminating in an orifice opening into the central opening of said cannula near the distal end thereof and in a direction transverse to the central axis on the cannula.

9. The cannula according to claim 8 wherein said orifices are located less than 5 mm. from the distal end of said cannula.

10. The cannula according to claim 9 wherein said fluid pumping means comprises:

a mechanical pump connected to a power source; and switch means connected between said pump and said power source for energizing said pump, thereby propelling the fluid through said four passages.

11. The cannula of claim 10, wherein said fluid pumping means includes means for pumping to said, four passages connected to said pumping means either a cleansing liquid, or a drying gas.

12. The cannula of claim 10, wherein at least one of said passages is connected to means for pumping cleansing liquid and at least one other of said passages is connected to means for pumping drying gas.

13. The cannula according to claim 8 wherein said fluid pumping means comprises:

a mechanical pump connected to a power source; and switch means connected between said pump and said power source for energizing said pump, thereby propelling the fluid through said four passages.

\* \* \* \* \*

UNITED STATES PATENT AND TRADEMARK OFFICE
CERTIFICATE OF CORRECTION

PATENT NO. : 6,017,333
DATED : January 25, 2000
INVENTOR(S) : Robert W. Bailey

Page 1 of 1

It is certified that error appears in the above-identified patent and that said Letters Patent is hereby corrected as shown below:

IN THE SPECIFICATION

Column 3,
Line 22, delete the words inner-Troca and substitute therefor -- cannula --

IN THE CLAIMS

Column 6,
Line 22, delete the words orifice is and substitute therefor -- orifices are --
Line 26, after the word "four" insert the word -- passages --

Signed and Sealed this

Seventeenth Day of July, 2001

*Attest:*

NICHOLAS P. GODICI
*Attesting Officer*   *Acting Director of the United States Patent and Trademark Office*